US006376549B1

(12) United States Patent
Fine et al.

(10) Patent No.: US 6,376,549 B1
(45) Date of Patent: Apr. 23, 2002

(54) METFORIMIN-CONTAINING COMPOSITIONS FOR THE TREATMENT OF DIABETES

(75) Inventors: Stuart A. Fine, Northbrook, IL (US); Kevin J. Kinsella, La Jolla, CA (US)

(73) Assignee: Akesis Pharmaceuticals, Inc., La Jolla, CA (US)

( * ) Notice: Subject to any disclaimer, the term of this patent is extended or adjusted under 35 U.S.C. 154(b) by 0 days.

(21) Appl. No.: 09/156,102

(22) Filed: Sep. 17, 1998

(51) Int. Cl.[7] .................... A61K 31/55; A61K 33/24; A61K 33/22; A01N 59/22
(52) U.S. Cl. .................... 514/635; 424/617; 424/626; 424/639; 424/655
(58) Field of Search ................. 424/646, 655, 424/682; 514/25, 162, 249, 255, 315, 331, 439, 440, 458, 592, 593, 635, 866

(56) References Cited

U.S. PATENT DOCUMENTS

| | | | |
|---|---|---|---|
| 4,921,877 A | 5/1990 | Cashmere et al. | 514/866 |
| 4,959,222 A | 9/1990 | Nadland et al. | 424/692 |
| 5,013,752 A | 5/1991 | Dobbins | 514/505 |
| 5,045,316 A | 9/1991 | Kaplan | 424/400 |
| 5,069,913 A | 12/1991 | Posner et al. | 424/646 |
| 5,087,623 A | 2/1992 | Boynton et al. | 514/188 |
| 5,087,624 A | 2/1992 | Boynton et al. | 514/188 |
| RE33,988 E | 7/1992 | Evans | 514/188 |
| 5,164,384 A | 11/1992 | Paul | 514/188 |
| 5,215,750 A | 6/1993 | Keane, II | 424/440 |
| 5,266,560 A | 11/1993 | Furman et al. | 514/4 |
| 5,300,496 A | 4/1994 | McNeill et al. | 514/186 |
| 5,308,627 A | 5/1994 | Umbdenstock, Jr. | 424/639 |
| 5,332,579 A | 7/1994 | Umbdenstock | 424/639 |
| 5,496,827 A | 3/1996 | Patrick | 514/310 |
| 5,527,790 A | 6/1996 | McNeill et al. | 514/186 |
| 5,532,269 A | 7/1996 | Koltringer | 514/440 |
| 5,543,405 A | 8/1996 | Keown | 514/188 |
| 5,550,113 A | 8/1996 | Mann | 514/54 |
| 5,597,585 A | 1/1997 | Williams et al. | 424/579 |
| 5,599,835 A | 2/1997 | Fisher | 514/440 |
| 5,614,224 A | 3/1997 | Womack | 424/646 |
| 5,620,967 A | 4/1997 | McNeill et al. | |
| 5,635,535 A | 6/1997 | Wagstaff | 514/557 |
| 5,637,324 A | 6/1997 | Bland | 424/655 |
| 5,641,531 A | 6/1997 | Liebrecht et al. | 426/583 |
| 5,651,900 A | 7/1997 | Keller et al. | 216/56 |
| 5,654,011 A | 8/1997 | Jackson et al. | 424/635 |
| 5,665,385 A | 9/1997 | Johnson et al. | 424/451 |
| 5,707,980 A | 1/1998 | Knutson et al. | 514/167 |
| 5,730,988 A | 3/1998 | Womack | 424/195.1 |
| 5,763,484 A | 6/1998 | Horrobin | 514/560 |
| 5,770,076 A | 6/1998 | Chu et al. | 210/490 |
| 5,770,215 A | 6/1998 | Moshyedi | 424/440 |
| 5,789,401 A | 8/1998 | McCarty | 514/188 |
| 5,797,898 A | 8/1998 | Santini, Jr. et al. | 604/890 |
| 5,798,042 A | 8/1998 | Chu et al. | 210/490 |
| 5,807,586 A | 9/1998 | Jackson et al. | 424/630 |
| 5,817,329 A | 10/1998 | Gardiner | 424/439 |
| 5,849,338 A | 12/1998 | Richardson et al. | 424/682 |
| 5,866,563 A | 2/1999 | McNeill et al. | 514/186 |
| 5,871,769 A | 2/1999 | Fleming et al. | 424/423 |
| 5,893,974 A | 4/1999 | Keller et al. | 210/483 |
| 5,905,075 A | 5/1999 | Harpe et al. | 514/188 |
| 5,908,647 A | 6/1999 | Golightly et al. | 426/74 |
| 5,962,030 A | * 10/1999 | Fine | 424/646 |
| 5,980,905 A | 11/1999 | De la Harpe et al. | 424/195.1 |

FOREIGN PATENT DOCUMENTS

| | | | |
|---|---|---|---|
| DE | 298 05 782 U1 | * | 10/1998 |
| EP | 0 561 744 A1 | | 9/1993 |
| EP | 0 834 318 | | 4/1998 |
| WO | WO 91/11117 | | 8/1991 |
| WO | WO 96/25939 | | 8/1996 |
| WO | WO 96/35421 | | 11/1996 |
| WO | WO 96/39871 | | 12/1996 |
| WO | WO 97/11614 | | 4/1997 |
| WO | WO 98/04248 | | 2/1998 |
| WO | WO 98/41113 | | 9/1998 |
| WO | WO 98/42211 | | 10/1998 |
| WO | WO 99/07387 | | 2/1999 |
| WO | WO 00/12095 | | 3/2000 |

OTHER PUBLICATIONS

Abbott et al., "The Impact of Diabetes on Survival Following Myocardial Infarction in Men vs Women," *JAMA*, 260(23):3456–3460 (1988).

ACC/AHA Task Force Report, "Guidelines for the Early Management of Patients With Acute Myocardial Infarction; A Report of the American College of Cardiology/American Heart Association Task Force on Assessment of Diagnostic and Therapeutic Cardiovascular Procedures (Subcommittee to Develop Guidelines for the Early Management of Patients With Acute Myocardial Infarction)," *JACC*, 16(2):249–292 (1990).

Anderson and Kozlovsky, "Chromium intake, absorption and excretion of subjects consuming self–selected diets," *The American Journal of Clinical Nutrition*, 41:1177–1183 (1985).

Anderson et al., "Urinary chromium excretion and insulinogenic properties of carbohydrates," *Am J Clin Nutr*, 51:864–868 (1990).

Gunnar et al., "Recommendations for Angioplasty After Intravenous Thrombolysis," *JAAC*, 16(2):249–292 (1990).

Stewart and Basten, "Lupus Erythematosus and Brain Scanning," *Annal of Internal Medicine*, 83(5):733–738 (1975).

(List continued on next page.)

Primary Examiner—Theodore J. Criares
(74) Attorney, Agent, or Firm—Foley, Hoag & Eliot LLP

(57) ABSTRACT

Compositions and methods using same for the treatment of diabetes its sequelae and pre-diabetic conditions are provided. Invention compositions include the anti-diabetic agent metformin, and bioavailable sources of one or more of chromium, vanadium and magnesium. Also provided are pharmaceutical agents containing invention compositions and methods for administering such agents.

40 Claims, No Drawings

OTHER PUBLICATIONS

Abraham et al., "The Effects of Chromium Supplementation on Serum Glucose and Lipids in Patients with and without Non–Insulin–Dependent Diabetes," Metabolism, 41(7):768–771 (1992).*

American Diabetes Association: "Nutrition Recommendations and Principles for People with Diabetes Mellitus," Diabetes Care, 19(1):S16–S19 (1996).*

American Diabetes Association: "Nutrition Recommendations and Principles for People with Diabetes Mellitus," Diabetes Care, 20(1):S14–S17 (1997).*

Blondel et al., "In Vivo Insulin Resistance in Streptozotocin–Diabetic Rates—Evidence for Reversal Following Oral Vanadate Treatment," Diabetologia 32:185–190 (1989).

Colwell, John A., "DCCT Findings: Applicability and Implications for NIDDM," Diabetes Reviews, 2(3):277–291 (1994).

Cunningham, John J., "Micronutrients as Nutriceutical Interventions in Diabetes Mellitus," Journal of the American College of Nutrition, 17(1):7–10 (1998).

Diabetes Pro Health Inc. "Pro Health Pak" (labels) Product described in label first sold no earlier than March of 1998.

Diabetes Pro Health Inc. "Pro Health Pak" (labels) Product described in label first sold no earlier than October of 1999.

Domingo et al., "Tiron administration minimizes the toxicity of vanadate but not its insulin mimetic properties in diabetic rats," Life Sciences (1992) 50/18 (1311–1317), XP000901833.

Dorman et al., "Double–Blind Evaluation of Efficacy and Tolerability of Metformin in NIDDM," Diabetes Care, 14(4):342–344 (1991).

Haffner et al., "Insulin Resistance Implications for Type II Diabetes Mellitus and Coronary Heart Disease," The American Journal of Medicine, 103:152–162 Aug. (1997).

Hansson et al., Effects of Intensive Blood–Pressure Lowering and Low–Dose Aspirin in Patients with Hypertension: Principal Results of the Hypertension Optimal Treatment (HOT) Randomised Trial, The lancelet, 351:1755–1762 Jun. (1998).

Inzucchi et al., "Efficacy and Metabolic Effects of Metformin and Troglitazone in Type II Diabetes Mellitus," The New England Journal of Medicine, 338(13):867–872 (1998).

Jovanovic–Peterson et al., "Chromium Supplementation for Gestational Diabetic Women (GDM) Improves Glucose Tolerance and Decreases Hyperinsulinemia," Diabetes, Abstract, 45(2) (1996).

Lardinois, Claude, "Type 2 Diabetes: Glycemic Targets and Oral Therapies for Older Patients," Geriatrics, 53(11):22–39 (1998).

Meyerovitch et al., "Oral Administration of Vanadate Normalizes Blood Glucose Levels in Streptozoticin–Treated Rats," The Jornal of Biological Chemistry, 262(14):6658–6662 (1987).

Pederson et al.,"Long–Term Effects of Vanadyl Treatment on Streptozocin–Induced Diabetes in Rats," Diabetes, 38:1390–1395 (1989).

Riales et al., "Effect of Chromium Chloride Supplementation on Glucose Tolerance and Serum Lipids Including High–Density Lipoproteins of adult Men," The American Journal of Clinical Nutrition, 34:2670–2678 (1981).

Schwartz et al., "Effect of Troglitazone in Insulin–Treated Patients with Type II Diabetes Mellitus," The New England Journal of Medicine, 338(13):861–866 (1998).

CA 127:257401, Mark et al., 1997.*

CA 127:199538, Haupt et al., 1997.*

CA 128:12817, Anderson et al., 1997.*

CA 124:194034, Zeigler et al., 1995.*

CA 123:282513, Pote et al., 1995.*

CA 120:235867, Verma et al., 1994.*

Aharon et al.;"Vanadyl Sulfate Does Not Enhance Insulin Action in Patients with Type I Diabetes", Diabetes Care 21 (12): 2194–2195 (Dec. 1998).

Amoikon et al.; "Effect of Chromium Tripicolinate on Growth, Glucose Tolerance, and Insulin Sensitivity, Plasma Metabobolites, and Growth Hormone in Pigs[1,2]", J. Anim. Sci. 73:1123–1130 (1995).

Anderson A. Richard, "Chromium, Glucose Intolerance and Diabetes" Journal of the American College of Nutrition 17 (6): 548–555 (1998).

Boyd et al. ; Combined Dietary Chromium Picolinate Supplementation and an Exercise Program Leads to a Reduction of Serum Cholesterol and Insulin in College–aged Subjects, J. Nutr. Biochem. 9: 471–475 (1998).

Cefalu et al.; "Effect of Chromium Picolinate on Insulin Sensitivity In Vivo", The Journal of Trace Elements in Experimental Medicine 12: 71–83 (1999).

Cheng et al.; "Follow–up Survey of People in China With Type 2 Diabetes Mellitus Consuming Supplemental Chromium", The Journal of Trace Elements in Experimental Medicine 12: 55–60 (1999).

Evans W. Gary, "The Effect of Chromium Picolinate on Insulin Controlled Parameters in Humans", Int. J. Biosocial Med. Research, 11(2): 163–180 (1989).

Jovanovic, et al.; "Chromium Supplementation for Women With Gestation al Diabetes Mellitus", The Journal of Trace Elements in Experimental Medicine 12: 91–97 (1999).

McCarty F. M. "Complementary Measures for Promoting Insulin Sensivitity in Skeletal Muscle", Medical Hypotheses 51: 451–464 (1998).

Perfetti et al.; "Non Therapeutic Strategies for the Treatment of Type 2 Diabetes", Diabetes/Metabolism Reviews 14: 207–225 (1998).

Preuss G. Harry, "Effects of Glucose/Insulin Perturbations on Aging and Chronic Disorders of Aging: The Evidence", Journal of the American College of Nutrition 16(5): 397–403 (1997).

Ravina et al.; "Reversal of Corticosteroid–induced Diabetes Mellitus with Supplemental Chromium", Diabetic Medicine 16: 164–167 (1999).

Spears J. W. "Reevaluation of the Metabolic Essentiality of the Minerals", J. Anim. Sci. 12(6): 1002–1008 (1999).

Ziegler et al.; "Treatment of Symptomatic Diabetic Peripheral Neuropathy with the Anti–oxidant α–Lipoic acid", Diabetologia 38: 1425–1433 (1995).

"Chromium Picolinate for Good Health?", Biolifeplus.com,, www.Biolifeplus.com/library/chromium.html, retrieved on Apr. 5, 2000.

Antiplatelet Trialists' Collaboration, "Collaborative overview of randomised trials of antiplatelet therapy–I: Prevention of death, myocardial infarction, and stroke by prolonged antiplatelet therapy in various categories of patients" BMJ 308:81–106 (1994).

Arsenian, M. A., "Magnesium and Cardiovascular Disease" *Progress in Cardiovascular Diseases* 35 (4):271–310 (1993).

Arsenian, M. A., "Magnesium and the Autonomic Nervous System" *Magnesium and Cardiovascular Disease* 291–310 (1993).

Avins, "Lowering Risk without Lowering Cholesterol: Implications for National Cholesterol Policy" *Annals of Internal Medicine* 125 (6):502–506 (1996).

Bailey, C. J, "Biguanides and NIDDM" *Diabetes Care* 15 (6):755–772 (1992).

Barnard, et al., "Diet and Exercise in the Treatment of NIDDM; The need for early emphasis" *Diabetes Care* 17 (12):1469–1472 (1994).

Bayraktar, M., "A Comparison of Acarbose Versus Metformin as an Adjuvant Therapy in Sulfonylurea–Treated NIDDM Patients" *Diabetes Care* 19 (3):252–254 (1996).

Bierman, E. L., "Atherogenesis in Diabetes" *Arteriosclerosis and Thrombosis* 12 (6):647–656 (1992).

Bloomgarden, Z. T., "American Diabetes Association Scientific Sessions, 1995; Magnesium Deficiency, Atherosclerosis, and Health Care" *Diabetes Care* 18 (12):1624–11627 (1995).

Caballero, "Vitamin E Improves the Action of Insulin" *Nutrition Reviews* 51 (11):339–340 (1993).

Calle–Pascual, A. L., "Comparison Between Acarbose, Metformin, and Insulin Treatment in Type 2 Diabetic Patients with Secondary Failure to Sulfonylurea Treatment" *Diabete & Metabolisme* (*Paris*) 21:256–260 (1995).

Cam, et al., "Long–term effectiveness of oral vanadyl sulphate in streptozotocin–diabetic rats" *Diabetologia* 36:218–224 (1993).

Clarke, R. J., "Suppression of Thromboxane $A_2$ but not of Systemic Prostacyclin by Controlled–Release Aspirin *The New England Journal of Medicine*" 325 (16):1137–1141 (1991).

Classen, H. G., "Magnesium and Potassium Deprivation and Supplementation in Animals and Man: Aspects in View of Intestinal Absorption" *Magnesium* 3:257–264 (1984).

Cohen and Kitzes, "Magnesium Sulfate and Digitalis–Toxic Arrhythmias" *JAMA* 249 (20):2808–2810 (1983).

Cohen, et al., "Oral Vanadyl Sulfate Improves Hepatic and Peripheral Insulin Sensitivity in Patients with Non–Insulin–dependent Diabetes Mellitus" *J. Clin. Invest.* 95:2501–2509 (1995).

Colwell, et al., "Correlation of Platelet Aggregation, Plasma Factor Activity, and Megathrombocytes in Diabetic Subjects With and Without Vascular Disease" *Metabolism* 26 (3):279–285 (1977).

Dai, et al., "One–year Treatment of Streptozotocin–Induced Diabetic Rats with Vanadyl Sulphate" *Pharmacology & Toxicology* 74:101–109 (1994).

Davì, et al., "Thromboxane $B_2$ Formation and Platelet Sensitivity to Prostacyclin in Insulin–Dependent and Insulin–Independent Diabetics" *Thrombosis Research* 26:359–370 (1982).

Davì, et al., "Thromboxane Biosynthesis and Platelet Function in Type II Diabetes Mellitus" *The New England Journal of Medicine* 322 (25):1769–1774 (1990).

Davies, et al., "Intramyocardial platelet aggregation in patients with unstable angina suffering sudden ischemic cardiac death" *Circulation* 73 (3):418–427 (1986).

Davis, et al., "Monotherapy with Magnesium Increases Abnormally Low High Density Lipoprotein Cholesterol: A Clinical Assay" *Current Therapeutic Research* 36 (2):341–346 (1984).

De Tata, et al., "Beneficial Effects of the Oral Administration of Vanadyl Sulphate on Glucose Metabolism in Senescent Rats" *Journal of Gerontology* 48 (5):B191–195 (1993).

DeFronzo, R. A., "Efficacy of Metformin in Patients with Non–Insulin–Dependent Diabetes Mellitus" *The New England Journal of Medicine* 33 (9):541–549 (1995).

Defronzo and Ferrannini, "Insulin Resistance; A Multifaceted Syndrome Responsible for NIDDM, Obesity, Hypertension, Dyslipidemia, and Atherosclerotic Cardiovascular Disease" *Diabetes Care* 14 (3):173–194 (1991).

Dieber–Rotheneder, et al., "Effect of oral supplementation with D–$\alpha$–tocopherol on the vitamin E content of Human low density lipoproteins and resistance to oxidation" *Journal of Lipid Research* 32:1325–1332 (1991).

Donadio, et al., "Platelet–Inhibitor Treatment of Diabetic Nephropathy: A 10–Year Prospective Study" *Mayo Clin Proc* 63:3–15 (1988).

Dubyak and Kleinzeller, "The Insulin–mimetic Effects of Vanadate in Isolated Rat Adipocytes" *The Journal of Biological Chemistry* 255 (11):5306–5213 (1980).

ETDRS Investigators, "Aspirin Effects on Mortality and Morbid in Patients With Diabetes Mellitus" *JAMA* 268 (10):2192–1300 (1992).

Ewald, et al., "Hypomagnesemia in Diabetic Children" *Acta Padiatr Scand* 72:367–371 (1983).

Expert Panel on Detection, Evaluation, and Treatment of High Blood Cholesterol in Adults, "Summary of the Second Report of the National Cholesterol Education Program (NCEP) Expert Panel on Detection, Evaluation, and Treatment of High Blood Cholesterol in Adults (Adult Treatment Panel II)" *JAMA* 269 (23):3015–3023 (1993).

Franz et al., "Nutrition Principles for the Management of Diabetes and Related Complications" *Diabetes Care* 17 (5):490–518 (1994).

Freund, et al., "Chromium Deficiency During Total Parenteral Nutrition" *JAMA* 241 (5):496–498 (1979).

Haffner, et al., "Cardiovascular Risk Factors in Confirmed Prediabetic Individuals; Does the Clock for Heart Disease Start Ticking Before the Onset of Clinical Diabetes?" *JAMA* 263 (21):2893–2988 (1990).

Haffner, et al., "Prospective Analysis of the Insulin–Resistance Syndrome (Syndrome X)" *Diabetes* 41:715–722 (1992).

Halberstam, et al., "Oral Vanadyl Sulfate Improves Insulin Sensitivity in NIDDM but Not in Obese Nondiabetic Subjects" *Diabetes* 45:659–666 (1996).

Harris, et al., "Onset of NIDDM Occurs at Lease 4–7 Yr Before Clinical Diagnosis" *Diabetes Care* 15 (7):815–819 (1992).

Hatwal, et al., "Association of hypomagnesemia with diabetic retinopathy" *Acta Ophthalmologica* 67:714–716 (1989).

Heath, et al., "Platelet Adhesiveness and Aggregation in Relation to Diabetic Retinopathy" *Diabetologia* 7:308–315 (1971).

Hennekens, et al., "An Overview of the British and American Aspirin Studies" *The New England Journal of Medicine* 318 (14):923–924 (1988).

Hermann, et al., "Therapeutic Comparison of Metformin and Sulfonylurea, Alone and in Various Combinations" *Diabetes Care* 17 (10):1100–1109 (1994).

Hirsh et al., "Aspirin and Other Platelet–Active Drugs; The Relationship Among Dose, Effectiveness, and Side Effects" *Chest* 108 (4):247S 257S (1995).

Jain, et al., "Some Metabolic Facets of Magnesium in Diabetes Mellitus" *Jr. Asso. Phys. Ind* 24:827–831 (1976).

Jarrett, et al., "The Bedford Survey: Ten Year Mortality Rates in Newly Diagnosed Diabetics, Borderline Diabetics and Normoglycaemic Controls and Risk Indices for Coronary Heart Disease in Borderline Diabetics" *Diabetologia* 22:79–84 (1982).

Jeejeebhoy, "Chromium deficiency, glucose intolerance, and neuropathy reversed by chromium supplementation, in a patient receiving long–term total parenteral nutrition" *The American Journal of Clinical Nutrition* 30:531–538 (1977).

Joffres, et al., "Relationship of magnesium intake and other dietary factors to blood pressure: the Honolulu heart study" *Am J Clin Nutr* 45:469–475 (1987).

Julkunen–Tütto and Tahvanainen, "The Effect of the Sample Preparation Method of Extractable Phenolics of Salicaceae Species" *Planta Medica* 55:55–61 (1989).

Kannel, W. B., "Lipids, diabetes, and coronary heart disease: Insights from the Framingham Study" *Am Heart J* 110 (5):1100–1107 (1985).

Kaplan, N. M., "The Deadly Quartet; Upper–Body Obesity, Glucose Intolerance, Hypertrigyceridemia, and Hypertension" *Arch Interrn Med* 149:1514–1520 (1989).

Klein, et al., "Visual Impairment in Diabetes" *Ophthalmology* 91 (1):1–9 (1984).

Koshinen, et al., "Coronary Heart Disease Incidence in NIDDM Patients In The Helsinki Heart Study" *Diabetes Care* 15 (7):820–825 (1992).

Krolewski, et al., "Evolving Natural History of Coronary Artery Disease in Diabetes Mellitus" *The American Journal of Medicine* 90 (suppl 2A):2A–56S–2A–61S (1991).

Krumholz, et al., "Aspirin for Secondary Prevention after Acute Myocardial Infarction in the Elderly: Prescribed Use and Outcomes" *Ann Intern Med* 124:292–298 (1996).

Kushi, et al., "Dietary Antioxidant Vitamins and Death From Coronary Heart Disease in Postmenopausal Women" *The New England Journal of Medicine* 334 (18):1156–1162 (1996).

Kuusisto, et al., "NIDDM and Its Metabolic Control Predict Coronary Heart Disease in Elderly Subjects" *Diabetes* 43:960–967 (1994).

Lee and Reasner, "Beneficial Effect of Chromium Supplementation on Serum Trigylceride Levels in NIDDM" *Diabetes Care* 17 (12):1449–1452 (1994).

Lee, et al., "Dose Effects of Aspirin on Gastric Prostaglandins Stomach Mucosal Injury" *Annals of Internal Medicine* 120 (3):184–189 (1994).

Levin, et al., "Tissue Magnesium Status in Diabetes Mellitus" *Diabetologia* 21:131–134 (1981).

Liu and Morris, "Relative chromium response as an indicator of chromium status" *The American Journal of Clinical Nutrition* 31:972–976 (1978).

Malabu, et al., "Effects of Chronic Vanadate Administration in the STZ–Induced Diabetic Rat; The Antihyperglycemic Action of Vanadate Is Attributable Entirely to Its Suppression of Feeding" *Diabetes* 43:9–15 (1994).

Margolis, et al., "Clinical Features of Unrecognized Myocardial Infarction—Silent and Symptomatic; Eighteen Year Follow–up: The Framingham Study" *The American Journal of Cardiology* 32 (1):1–7 (1973).

Marier, J. R., "Cardio–Protective Contribution of Hard Waters to Magnesium In–Take" *Rev. Can. Biol.* 37 (2):115–125 (1978).

Mather, et al., "Hypomagnesaemia in Diabetes" *Clinica Chimica Acta* 95:235–242 (1972).

McNair, et al., "Hypomagnesemia, a Risk Factor in Diabetic Retinopathy" *Diabetes* 27:1075–1077 (1978).

McNair, et al., "Renal hypomagnesaemia in human diabetes mellitus: its relation to glucose homeostasis" *European Journal of Clinical Investigation* 12:81–85 (1982).

McNeill, et al., "Oral Vanadium and Lowering of Blood Glucose" *Diabetes* 43:1268 (1994).

McPhillips, et al., "Cardiovascular Disease Risk Factors Prior to the Diagnosis of Impaired Glucose Tolerance and Non–Insulin–Dependent Diabetes Mellitus in a Community of Older Adults" *American Journal of Epidemiology* 131 (3):443–453 (1990).

Meinert, et al., "Mortality Results; *A Study of the Effects of Hypoglycemic Agents on Vascular Complications in Patients with Adult–Onset Diabetes*" *The University Group Diabetes Program* Chptr II:786–830 (1961).

Mertz, W., "Effects and Metabolism of Glucose Tolerance Factor" *Nutrition Reviews* 33 (5):129–135 (1975).

Mongold, et al., "Toxicological Aspect of Vanadyl Sulphate on Diabetic Rats: Effects on Vanadium Levels and Pancreatic B–Cell Morphology" *Pharmacology & Toxicology* 67:192–198 (1990).

Mooradian, A. D., "Selected Vitamins and Mineral in Diabetes" *Diabetes Care* 17 (5):464–479 (1994).

Morris, et al., "Correlations between Abnormalities In Chromium and Glucose Metabolism In a Group of Diabetics" *Clinical Chemistry* 34 (7):1525–1526 (1988).

Morris, et al., "Effect of Glucose Loading on Concentrations of Chromium in Plasma and Urine in Healthy Adults" *Clinical Chemistry* 34 (6):1114–1116 (1988).

Morris, et al., "Plasma Chromium and Chromium Excretion in Diabetes" *Clinical Chemistry* 31 (2):334–335 (1985).

Nadler, et al., "Intracellular Free Magnesium Deficiency Plays a Key Role in Increased Platelet Reactivity in Type II Diabetes Mellitus" *Diabetes Care* 15 (7):835–841 (1992).

Newman, et al., "Serum Chromium and Angiographically Determined Coronary Artery Disease" *Clin. Chem.* 24 (4):541–544 (1978).

Offenbacher and Pi–Sunyer, "Beneficial Effect of Chromium–rich Yeast on Glucose Tolerance and Blood Lipids in Elderly Subjects" *Diabetes* 29:919–925 (1980).

Orchard and Strandness, "Assessment of Peripheral Vascular Disease in Diabetes" *Circulation* 88 (2):819–828 (1993).

Pagano, G. "Metformin Reduces Insulin Requirement in Type 1 (Insulin–Dependent) Diabetes" *Diabetologia* 24:351–354 (1983).

Paolisso et al., "Dietary magnesium supplements improve B–cell response to glucose and arginine in elderly non–insulin dependent diabetic subjects" *Acta Endocrinologica* 121:16–20 (1989).

Paolisso, et al., "Daily Vitamin E Supplements Improve Metabolic Control But Not Insulin Secretion in Elderly Type II Diabetic Patients" *Diabetic Care* 16 (11):1434–1437 (1993).

Paolisso, et al., "Improved Insulin Response and Action by Chronic Magnesium Administration in Aged NIDDM Subjects" *Diabetes Care* 12 (4):265–69 (1989).

Paolisso, et al., "Magnesium and glucose homeostasis" *Diabetologia* 33:511–514 (1990).

Paolisso, et al., "Pharmacologic doses of vitamin E improve insulin action in healthy subjects and non–insulin–dependent diabetic patients" *Am J Clin Nutr* 57:650–656 (1993).

Potter, et al., "Glucose Metabolism in Glucose–Intolerant Older People During Chromium Supplementation" *Metabolism* 34 (3):199–204 (1985).

Press, et al., "The Effect of Chromium Picolinate on Serum Cholesterol and Apolipoprotein Fractions in Human Subjects" *West J Med* 152:41–45 (1990).

Reaven, G. M., "Role of Insulin Resistance in Human Disease" *Diabetes* 37:1595–1607 (1988).

Reinhart, R. A., "Magnesium Metabolism; A Review With Special Reference to the Relationship Between Intracellular Content and Serum Levels" *Arch Intern Med* 148:2415–2420 (1988).

Resnick, et al., "Hypertension and Peripheral Insulin Resistance; Possible Mediating Role of Intracellular Free Magnesium" *The American Journal of Hypertension* 3 (5) (Part 1):373–379 (1990).

Resnick, L. M., "Cellular Calcium and Magnesium Metabolism in the Pathophysiology and Treatment of Hypertension and Related Metabolic Disorders" *The American Journal of Medicine* 93 (Suppl 2A):2A–11S 2A–20S (1992).

Rimm, et al., "Vitamin E and Risk of Coronary Heart Disease in Men" *The New England Journal of Medicine* 328 (20):1453–1456 (1993).

Roeback, et al.,"Effects of Chromium Supplementation on Serum High–Density Lipoprotein Cholesterol Levels in Men Taking Beta–Blockers" *Annals of Internal Medicine* 115 (12):917–924 (1991).

Rubin, et al., "Health Care Expenditures for People with Diabetes Mellitus, 1992" *Journal of Clinical Endocrinology and Metabolism* 78 (4):809A–809F (1994).

Rude, R. K., "Physiology of Magnesium Metabolism and the Important Role of Magnesium in Potassium Deficiency" *The American Journal of Cardiology* 63:31G–34G (1989).

Ryzen, et al., "Low blood mononuclear cell magnesium in intensive cardiac care unit patients" *American Heart Journal* 111:475–480 (1986).

Saad, et al., "Sequential Changes in Serum Insulin and Concentration During Development of Non–Insulin–Dependent Diabetes" *The Lancet* pp 1356–1359 (1989).

Salonen, et al., "Increased risk of non–insulin dependent diabetes mellitus at low plasma vitamin E concentrations: a four year follow up study in men" *BMJ* 311:1124–1127 (1995).

Saltiel and Olefsky, "Thiazolidinediones in the Treatment of Insulin Resistance and Type II Diabetes" *Diabetes* 45:1661–1669 (1996).

Seelig and Heggtveit, "Magnesium interrelationships in ischemic heart disease: a review" *The American Journal of Clinical Nutrition* 27:59–79 (1974).

Seelig, M., "Cardiovascular Consequences of Magnesium Deficiency and Loss: Pathogenesis, Prevalence and Manifestations—Magnesium and Chloride Loss in Refractory Potassium Repletion" *The American Journal of Cardiology* 63:4G–21G (1989).

Sjögren, et al., "Magnesium, Potassium and Zinc Deficiency in Subjects with Type II Diabetes Mellitus" *Acta Med Scand* 224:461–465 (1988).

Sjögren, et al., "Oral Administration of Magnesium Hydroxide to Subjects with Insulin–Dependent Diabetes mellitus: Effects on Magnesium and Potassium Levels and on Insulin Requirements" *Magnesium* 7:117–122 (1988).

Stamler, et al., "Diabetes, Other Risk Factors, and 12–Yr Cardiovascular Mortality for Men Screened in the Multiple Risk Factor Intervention Trial" *Diabetes Care* 16 (2):434–444 (1993).

Stampfer, et al., "Vitamin E Consumption and the Risk of Coronary Disease in Women" *The New England Journal of Medicine* 328 (20):1444–1449 (1993).

Steinberg, et al., "Antioxidants in the Prevention of Human Atherosclerosis" *Circulation* 85 (6):2337–2345 (1992).

Steinberg, et al., "Beyond Cholesterol; Modifications of Low–Density Lipoprotein That Increase Its Atherogenicity" *The New England Journal of Medicine* 320 (14):915–924 (1989).

Stephens, et al., "Randomised controlled trial of vitamin E in the patients with coronary disease: Cambridge Heart Antioxidant Study (CHAOS)" *The Lancet* 347:781–786 (1996).

The RISC Group, "*Medicine Science;* Risk of myocardial infarction and death during treatment with low dose aspirin and intravenous heparin in men with unstable coronary artery disease" *The Lancet* 336:827–830 (1990).

The SALT Collaborative Group, "Swedish Aspirin Low––dose Trial (SALT) of 75 mg aspirin as secondary prophylaxis after cerebrovascular ischaemic events" *The Lancet* 338 (8779):1345–1349 (1991).

Thompson, et al., "Studies of Vanadyl Sulfate as a Glucose–Lowering Agent in STZ–Diabetic Rats" *Biochemical and Biophysical Research Communications* 197 (3):1549–1555 (1993).

Tosiello, L., "Hypomagnesemia and Diabetes Mellitus" *Arch Intern Med* 156:1143–1148 (1996).

Trip, et al., "Platelet Hyperreactivity and Prognosis in Survivors of Myocardial Infarction" *The New England Journal of Medicine* 322 (22):1549–1554 (1990).

Tuman and Doisy, "Metabolic Effects of the Glucose Tolerance Factor (GTF) in Normal and Genetically Diabetic Mice" *Diabetes* 26 (9):820–826 (1977).

United Kingdom Prospective Diabetes Study Group, "United Kingdom prospective diabetes study (UKPDS) 13: relative efficacy of randomly allocated diet, sulphonylurea, insulin, or metform in patients with newly diagnosed non––insulin dependent diabetes followed for three years" *BMJ* 310:83–88 (1995).

Verlangieri and Bush, "Effects of d–α–Tocopherol Supplementation on Experimentally Induced Primate Atherosclerosis" *Journal of the American College of Nutrition* 11 (2):131–138 (1992).

Whang, R., "Magnesium Deficiency: Pathogenesis, Prevalence, and Clinical Implications" *The American Journal of Medicine* 82 (suppl 3A):24–29 (1987).

Widman, "The Dose–Dependent Reduction in Blood Pressure Through Administration of Magnesium; A Double Blind Placebo Controlled Cross–Over Study" *The American Journal of Hypertension, Inc.* 6:41–45 (1993).

Woods and Fletcher, "Long–term outcome after intravenous magnesium sulphate in suspected acute myocardial infarction: the second Leicester Intravenous Magnesium Intervention Trial (LIMIT–2)" The Lancet 343:816–819 (1994).

Woolliscroft and Barbosa, "Analysis of Chromium Induced Carbohydrate Intolerance in the Rat" J. Nutr. 107:1702–1706 (1977).

Anderson et al., "Elevated Intakes of Supplemental Chromium Improve Glucose and Insulin Variables in Individuals With Type 2 Diabetes", Diabetes 46:1786–1791 (1997).

Cerulli et al., "Chromium Picolinate Toxicity", The Annals of Pharmacotherapy 32:428–431, (Apr. 1998).

Chowdhury and Lasker, "Elevated glycated haemoglobin in non–diabetic patients is associated with an increased mortality in myocardial infarction", Postgrad. Med. J. 74: 480–481 (1998).

ChromeMate: Research Summary. (1993).

Dehghani et al., "Effect of Vanadyl Sulphate on Glucose Homeostasis in Severe Diabetes Induced by Streptozotocin in Rats", Indian J. Med Res. 106: 481–585 (1997).

Diabetes Pro Health Inc., "Introducing A Nutritional Supplement Specifically Formulated For Adults With Diabetes & Pre–Diabetes" (1997).

Diabetes Pro Health Inc. "Pro Health Pak" (labels) Product described in label first sold no earlier than June of 1997.

Diabetes Pro Health "Akesis Pharmaceuticals Inc". (Pamphlet) Product first used no earlier than June of 1997.

Domingo et al., "Administration of Vanadyl Sulfate by Gavage does not Normalize Blood Glucose Lvels in Streptozotocin–induced Diabetic Rats", Research Communications in Chemical Pathology and Pharmacology 75 (3) : 369–372 (Mar. 1992).

E. B. Opkere et al., "Future of oral metavanadate to correct streptozotocin–induced diabetes in rats", Diabetic Medicine Supplement 2 to vol. 5: A30 (p.8) (1988) (Abstract).

Evans and Pouchnik, "Composition and Biological Activity of Chromium–Pyridine Carboxylate Complexes", Journal of Inorganic Biochemistry 49 :177–187 (1993).

Evans and Bowman, "Chromium Picolinate Increases Membrane Fluidity and Rate of Insulin Internalization", Journal of Inorganic Biochemistry 46: 243–250 (1992).

Evans, W. G., "The Effect of Chromium Picolinate on Insulin Controlled Parameters in humans", Int. J. Biosocial Med. Research 11 (2): 163–180 (1989).

Foot et al., "The Effects of Orthovanadate, Vanadyl and Peroxides of Vanadate on Glucose Metabolism in Skeletal Muscle Preparations in Vitro" Molecular and Cellular Biochemistry 109; 157–162 (1992).

Grant et al., "Chromium and Exercice Training: effect on obese women", Medicine & Science in Sports & Exercice, pp. 992–998 (1997).

InterHealth Company., "Facts About Chromium Nutrition; Fact Sheet #1: The Importance of Niacin–Bound Chromium in Human Nutrition", (Jul. 21, 1992).

InterHealth Company., "Facts About Chromium Nutrition; Fact Sheet #2: Niacin–Bound Chromium Compounds Vary; ChromeMate's Oxygen–Coordinated Complex Found 18 Times More Potent", (Oct. 5, 1992).

InterHealth Company., "Facts About Chromium Nutrition; Fact Sheet #3 : UC Study finds ChromeMate More Biovalaible than Chromium Picolinate, Chromium Chloride" (Oct. 14, 1992).

Lefavi et al., "Lipid–Lowering Effect of a Dietary Nicotinic Acid—Chromium(III) Complex in Male Athletes", The FASEB Journal, 5 (6) A1645 (1991) (Abstract).

Pote et al. "An Antitherogenic role for folic acid in experimental Diabetes", J. Clin. Biochem. Nutr. 18(3):157–164 (1995).(Abstract).

Malabu et al., "Effects of Chronic Vanadate Administration in The STZ–Induced Diabetic Rat", Diabetes 43:9–15 (Jan. 1994).

Moore and Friedl, "Physiology of Nutritional Supplements: Chromium Picolinate and Vanadyl Sulfate", National Strength and Condioning Association Journal 14:(3) 47–48 (1992).

Olin et al., "Comparative Retention/Absorption of Chromium (Cr) from Cr Chloride(CrCl), Cr Nicotinate (CrNic), and Cr Picolinate (CrPic) in a Rat model", (Reprint of Abstract Data Presented at $33^{rd}$ Annual Meeting of the American College of Nutrition, Oct. 10, 1992).

Preuss et al., "Effects of Different Chromium Compounds on Blood Pressure and Lipid Peroxidation in Spontaneously Hypertensive Rats", Clinical Nephrology 47(5) 325–330 (1997).

Ravina et al., "Clinical Use of the Trace Element Chromium (III) in the Treatment of Diabetes Mellitus", The Journal of Trace Elements in Experimental Medicine 8:183–190 (1995).

Stearns et al., "Chromium (III) picolinate produces chromosome damage in Chinese hamster ovary cells $^{1}$", The FASEB Journal 9:1643–1649 (Dec. 1995).

Thomas and Gropper,. "Effect of Chromium Nicotinic Acid Supplementation on Selected Cardiovascular Disease Risk Factors", Biological Trace Element Research 55(3): 297–305 (1996).

Tomlinson, "Future Prevention and Treatment of Diabetic Neuropathy", Diabetes & Metabolism(Paris)24 (Suppl. 3): 79–83 (1998).

Urberg et al., "Hypocholesterolemic Effects of Nicotinic Acid and Chromium Supplementation", The Journal of Family Practice 27:(6) 603–606 (1988).

Urberg and Zemel., "Evidence for Synergism Between Chromium and Nicotinic Acid in the Control of Glucose Tolerance in Elderly Humans", Metabolism 36(9): 896–899 (Sep. 1987).

Walter et al., "The Effect of Oral Chromium Picolinate on Glycemic Responses and Lipid Profiles in Patients with Type II Diabetes Mellitus", Diabetes 42 (Suppl.) :146(May 1993).

Wilson and Gondy., "Effects of Chromium Supplementation on Fasting Insulin Levels and Lipid Parameters in Healthy, Non–obese Young Subjects", Diabetes Research and Clinical Practice 28: 179–184 (1995).

Ziegler et al., "Treatment of Symptomatic Diabetic Peripheral Neuropathy with the anti–oxidant α–lipoic acid", Diabetologia 38: 1425–1433 (1995).

* cited by examiner

METFORIMIN-CONTAINING COMPOSITIONS FOR THE TREATMENT OF DIABETES

FIELD OF THE INVENTION

This invention relates to pharmaceutical compounds formulated in conjugation with dietary supplements; and to methods of using the resulting compositions for the treatment of a number of conditions. Particularly, this invention relates to metformin-containing pharmaceutical compositions and to methods of using the same for the treatment of diabetes and a number of symptoms which precede and/or accompany diabetes.

BACKGROUND OF THE INVENTION

Diabetes mellitus is a mammalian condition in which the amount of glucose in the blood plasma is abnormally high. Elevated glucose levels in some instances can lead to higher than normal amounts of a particular hemoglobin, HbA1c. This condition can be life-threatening and high glucose levels in the blood plasma (hyperglycemia) can lead to a number of chronic diabetes syndromes, for example, atherosclerosis, microangiopathy, kidney disorders or failure, cardiac disease, diabetic retinopathy and other ocular disorders, including blindness.

Diabetes mellitus is known to affect at least 10 million Americans, and millions more may unknowingly have the disease. There are two forms of the disease. In the form of this disease known as Type II, non-insulin dependent diabetes (NIDDM) or adult-onset (as opposed to juvenile diabetes or Type I), the pancreas often continues to secrete normal amounts of insulin. However, this insulin is ineffective in preventing the symptoms of diabetes which include cardiovascular risk factors such as hyperglycemia, impaired carbohydrate (particularly glucose) metabolism, glycosuria, decreased insulin sensitivity, centralized obesity hypertriglyceridemia, low HDL levels, elevated blood pressure and various cardiovascular effects attending these risk factors. Many of these cardiovascular risk factors are known to precede the onset of diabetes by as much as a decade. These symptoms, if left untreated, often lead to severe complications, including premature atherosclerosis, retinopathy, nephropathy, and neuropathy. Insulin resistance is believed to be a precursor to overt NIDDM and strategies directed toward ameliorating insulin resistance may provide unique benefits to patients with NIDDM.

Current drugs used for managing Type II diabetes and its precursor syndromes, such as insulin resistance, fall within five classes of compounds: the biguanides, thiazolidinediones, the sulfonylureas, benzoic acid derivatives and α-glucosidase inhibitors. The biguanides, e.g., metformin, are believed to prevent excessive hepatic gluconeogenesis. The thiazolidinediones are believed to act by increasing the rate of peripheral glucose disposal. The sulfonylureas, e.g., tolbutamide and glyburide, the benzoic acid derivatives, e.g. repaglinide, and the α-glucosidase inhibitors, e.g. acarbose, lower plasma glucose primarily by stimulating insulin secretion.

Among biguanides useful as diabetic therapeutic agents, metformin has proven particularly successful. Metformin is an anti-diabetic agent that acts by reducing glucose production by the liver and by decreasing intestinal absorption of glucose. It is also believed to improve the insulin sensitivity of tissues elsewhere in the body (increases peripheral glucose uptake and utilization). Metformin improves glucose tolerance in impared glucose tolerant (IGT) subjects and NIDDM subjects, lowering both basal and postprandial plasma glucose.

Unlike sulfonylureas, metformin does not produce hypoglycemia in either diabetic or non-diabetic subjects. With metformin therapy, insulin secretion remains unchanged while fasting insulin levels and day-long plasma insulin response may decrease. Metformin also has a favorable effect on serum lipids, which are often abnormal in NIDDM patients. In clinical studies, particularly when baseline levels of lipids were abnormally elevated, metformin lowered mean fasting serum triglycerides, total cholesterol, and LDL cholesterol levels and had no adverse effects on other lipid levels.

Currently, there is no composition for the treatment of diabetes, its precursor syndromes and related sequelae that combines metformin with bioavailable elemental nutritional supplements such as vanadium, magnesium and chromium as well as other non-elemental nutritional palliatives which are effective in managing diabetes, its precursors, and sequelae.

DESCRIPTION OF THE INVENTION

The present invention provides for metformin-containing compositions containing one or more nutritional supplements in an amount sufficient to produce a desirable effect, such as bioavailable sources of vanadium, chromium, magnesium, vitamin E, lipoic acid, folate and the like. Additionally, compositions of the present invention may contain aspirin. The present invention improves upon current regimens for treating diabetes with metformin, by exploiting the insulin-like effects of vanadium and chromium and also by providing a source of magnesium, which is so often deficient in people with diabetes. Also provided are methods for the treatment of diabetes and conditions attending or commonly preceding diabetes, comprising administration of an effective amount of the aforementioned compositions.

DETAILED DESCRIPTION OF THE INVENTION

In accordance with the present invention, there are provided compositions comprising metformin, one or more of a bioavailable source of chromium, vanadium or magnesium and pharmaceutically acceptable salts thereof; and a physiologically acceptable carrier.

In another aspect of the present invention, there are provided compositions comprising, in addition to the aforementioned components, an effective amount of one or more additional anti-diabetic agents such as insulin, a thiazolidinedione, a sulfonylurea, a benzoic acid derivative, an α-glucosidase inhibitor, exendin-4, or the like. As will be appreciated by those skilled in the art, the effective amount of each of these components will vary by the patient and severity of condition being treated. Thus, any determination as to the effective amount will be made by the treating professional.

Metformin (N,N-dimethylimidodicarbonimidicdiamide; 1,1-dimethylbiguanide; N,N-dimethylbiguanide; N,N-dimethyldiguanide; N'-dimehtylguanylguanidine) is commonly administered as metformin HCl. This as well as all other useful forms of metformin are contemplated for use in the practice of the present invention. Generally, a fixed dosage regimen is individualized for the management of hyperglycemia in diabetes mellitus with metformin HCl or any other pharmacologic agent. Individualization of dosage is made on the basis of both effectiveness and tolerance, while generally not exceeding the maximum recommended daily dose of 2550 mg. In one embodiment of the present invention, compositions comprise in the range of about 100 mg up to about 2550 mg per daily dose. In some embodiments of the invention, doseages may be less than 100 mg per day when administered with higher amounts of bioavailable forms of two or more of chromium, vanadium or magnesium.

Thiazolidinediones contemplated for use in the practice of the present invention include troglitazone, and the like. Effective amounts of troglitazone, when used alone, range from about 10 mg up to about 800 mg per daily dose and a commensurate range is contemplated for use in the present invention. In a preferred aspect of the present invention, the composition comprises from about 100 mg to about 600 mg of troglitazone per daily dose.

As readily recognized by those of skill in the art, a variety of sulfonylureas are useful for the treatment of diabetes. Exemplary sulfonylureas contemplated for use in the practice of the present invention (with typical daily dosages indicated in parentheses) include acetohexamide (in the range of about 250 up to about 1500 mg), chlorpropamide (in the range of about 100 up to about 500mg), tolazimide (in the range of about 100 up to about 1000 mg), tolbutamide (in the range of about 500 up to about 3000 mg), gliclazide (in the range of about 80 up to about 320 mg), glipizide (in the range of about 5 up to about 40 mg), glipizide GITS (in the range of about 5 up to about 20 mg), glyburide (in the range of about 1 up to about 20 mg), micronized glyburide (in the range of about 0.75 up to about 12 mg), glimeperide (in the range of about 1 up to about 4 mg), and the like.

As readily recognized by those of skill in the art, a variety of alpha-glucosidase inhibitors are useful for the treatment of diabetes. Exemplary alpha-glucosidase inhibitors contemplated for use in the practice of the present invention include acarbose, miglitol, and the like. Effective dosages of both acarbose and miglitol are in the range of about 75 up to about 300 mg daily.

As readily recognized by those of skill in the art, a variety of benzoic acid derivatives are useful for the treatment of diabetes. Exemplary benzoic acid derivatives contemplated for use in the practice of the present invention include repaglinide (effective daily dosage in the range of about 0.5 mg up to about 16 mg), and the like.

Exendin-4, its derivatives and simlirar proteins are also contemplated for use in the practice of the present invention. Although exendin-4 is still under study, it is anticipated that the action and effects of exendin-4, like those of other anti-diabetic agents, will be enhanced by the ability of exendin-4 to enhance insulin secretion and reduce glucagon secretion when included in invention formulations and administered as part of a supervised regimen of therapy.

It has been discovered that administration of bioavailable forms of nutritional supplements such as chromium, vanadium, and magnesium are able to alleviate one or more symptomologies associated with diabetes or which indicate a predisposition to diabetes. As will be understood by those skilled in the art, "bioavailable," as used herein, conotes that a particular element or compound is, for example by its particular oxidation state or the components with which it is complexed, in a form which allows for the element or compound to be absorbed, incorporated or be otherwise physiologically available by the individual to whom it is administered. Any bioavailable sources of the elements chromium, vanadium and magnesium are contemplated for use in the practice of the present invention.

Bioavailable sources of vanadium, such as vanadyl sulfate, and of chromium, such as chromium picolinate, have properties that closely mimic, as well as enhance, many of the physiological effects of insulin because it has been found that these elements serve to both increase the effectiveness and enhance the anabolic effects of insulin. Supplementation of these elements into a normal diet increases lean body mass without increasing body fat, stabilize blood sugar levels, increases the responsiveness of cells to insulin, and lowers blood lipid and cholesterol levels. By their ability to potentiate the effects of insulin, both vanadyl sulfate and chromium have been found to enhance the entry of glucose (for energy) and amino acids (for protein synthesis) into muscle cells and to inhibit the action of enzymes that catabolize the amino acids and proteins. In addition, these particular elements include cholesterol lowering, energy producing and anabolic promoting properties.

The combination of vanadate and chromium enhances the ability of insulin to utilize glucose. Vanadate ions, like insulin, stimulate glucose transport, activate glycogen synthase, increase glycogen syntheses in fat cells, and stimulate carbohydrate uptake in the liver. Glycogen synthase is an enzyme that causes the conversion of glucose into glycogen, a polysaccharide that is the chief carbohydrate storage material in humans. The maximum level of glycogen synthase activation produced by vanadate is indistinguishable from that of insulin. Thus, the presence of in-vivo vanadate can lead to improved glucose metabolism and enhance the effects of natural or administered levels of insulin.

Chromium, like vanadium, possesses properties that both mimic and enhance the effects of insulin. Chromium enhances the effects of insulin by indirectly assisting amino acid uptake by muscle, stimulating protein synthesis, and retarding the rate of protein breakdown. Chromium also lowers serum triglycerides. Yet, many clinical studies utilizing chromium as a nutritional supplement have shown only modest improvements in glucose tolerance due to poor absorption of nutritional (trivalent) chromium. In this respect, trivalent chromium has a strongly positive charge that impedes its movement across cell membranes. Due to the presence of competing ions such as copper, iron, manganese and zinc in the human body, adequate absorption of chromium occurs best when the metal is associated with a chelating agent such as picolinic acid. Because of its unique structure, picolinic acid binds tightly to transition metals such as zinc, manganese, and chromium, thereby neutralizing their positive charges and expediting their movement across cell membranes. Thus, compounds such as chromium picolinate and/or chromium polynicotinate are particularly useful as bioavailable chromium sources.

Trivalent chromium is an essential micronutrient required mainly for maintenance of normal glucose tolerance. Bioavailable sources of chromium include one or more of chromium picolinate, chromium polynicotinate, as well as other bioavailable forms of chromium known in the art or developed in the future, particularly forms of chromium that are chelated to an organic anion thus forming a membrane permeable complex that is more permeable than chromium alone. In one embodiment of the present invention, in the range of about 10 $\mu$g up to about 400 $\mu$g of elemental chromium equivalent is present per daily dose. As used herein "elemental chromium equivalent" refers to the amount of elemental chromium present in the particular complex (e.g. chromium picolinate) chosen for a given formulation of invention compositions. In one embodiment of the present invention, in the range of about 30 $\mu$g up to about 5000 μg chromium picolinate and/or chromium polynicotinate is present per daily dose. In another embodiment of the present invention, in the range of about 200 μg up to about 4000 μg chromium picolinate and/or chromium polynicotinate is present per daily dose. In a preferred embodiment, about 3264 μg of chromium picolinate and/or chromium polynicotinate is present per daily dose.

Vanadium is a group V transition element that exists in several oxidation states (+2, +3, +4, and +5). Both vanadyl (+4) and vanadate (+5) may be used to alleviate diabetic and pre-diabetic symptomology, with the vanadyl form being better tolerated physiologically. Bioavailable sources of vanadium include vanadyl sulfate, as well as other bioavailable forms of vanadium known in the art or developed in the future, particularly forms of vanadium that are chelated to an organic anion thus forming a membrane permeable complex that is more permeable than vanadium alone. In one embodiment of the present invention, vanadyl sulfate is present in the range of about 50 mg up to about 7500 mg, per daily dose. In another embodiment of the present invention, vanadyl sulfate is present in the range of about 75 mg up to about 5000 mg, per daily dose. In another embodiment of the present invention, vanadyl sulfate is present in the range of about 20 mg up to about 100 mg, per daily dose.

Magnesium is a necessary intercellular co-factor for many enzymes and plays an essential role in protein synthesis. The magnesium ion (+2) plays a fundamental role in carbohydrate metabolism, and in the action of insulin in particular. Moreover, there is a link between Mg depletion and ischemic heart disease. Magnesium supplementation reduces platelet reactivity in NIDDM patients, reduces the incidence of congestive heart failure and death in those with acute myocardial infarction, improves glucose metabolism, improves insulin sensitivity, and reduces lipid abnormalities. Magnesium supplementation also reduces systolic and diastolic blood pressure.

A bioavailable source of magnesium is magnesium chloride. Magnesium may also be optionally complexed with a suitable complex such as citrate, fumarate, malate, glutarate, and succinate, as well as other bioavailable forms of magnesium known in the art or developed in the future, particularly forms of magnesium that are chelated to an organic anion thus forming a membrane permeable complex that is more permeable than magnesium alone. In one embodiment of the present invention, elemental magnesium equivalent is present in the range of about 10 mg up to about 3 g, per daily dose. As used herein "elemental magnesium equivalent" refers to the amount of bioavailable magnesium present in the particular complex (e.g. magnesium chloride) chosen for a given formulation of invention compositions. In another embodiment of the present invention, elemental magnesium equivalent is present in the range of about 10 mg up to about 60 mg, per daily dose. In another embodiment of the present invention, elemental magnesium equivalent is present in the range of about 60 mg up to about 1500 mg, per daily dose. In yet another embodiment of the present invention, magnesium chloride is present in the range of about 100 mg up to about 200 mg, per daily dose. In still another embodiment of the present invention, magnesium chloride is present in the range of about 200 mg up to about 500 mg, per daily dose. In a preferred embodiment of the present invention, magnesium chloride is present at about 384 mg, per daily dose.

As will be understood by those skilled in the art, other bioavailable sources of the foregoing elements exist or may become available and will be suitable for use in the practice of the present invention.

In one embodiment, the composition of the present invention further optionally comprises, one or more of aspirin or willow bark extracts, a bioavailable source of vitamin E, a bioavailable source of lipoic acid and/or a bioavailable source of folic acid.

Any source of aspirin (acetyl salicylic acid) is suitable for use in compositions of the present invention. Aspirin may be employed with or without the use of physiologically acceptable buffering agents commonly used to minimize the propensity of aspirin to interfere with the gastrointestinal mucosa. Wide ranging dosages of aspirin are typically employed and the present invention may be practiced with any pharmaceutically and physiologically acceptable amount. In one embodiment of the present invention, when aspirin is included in invention compositions, a daily dose of the composition will contain in the range of about 1 mg up to about 650 mg of aspirin. In another embodiment, a daily dose of the present composition will contain in the range of about 20 mg up to about 80 mg of aspirin. In yet another embodiment, a daily dose of the present composition will contain in the range of about 80 mg up to about 650 mg of aspirin. In a preferred embodiment, a daily dose of the present composition will contain about 20 mg of aspirin.

Vitamin E improves the action of insulin, glucose metabolism and lipid levels. People with diabetes have been shown to have reduced plasma vitamin E concentrations. As many as 60% of the newly diagnosed diabetic patients also have clinically obvious cardiovascular disease which may be alleviated by the ability of vitamin E to reduce artherosclerosis. Although the exact mechanism by which vitamin E exerts its effects on insulin use is unknown, it is postulated that the effects are the result of the well known antioxidant properties of vitamin E inasmuch as administration of vitamin E has been shown to reduce oxidative stress. Daily oral supplements of vitamin E has been shown to result in strong increase in total glucose disposal and in non-oxidative glucose metabolism in people with diabetes.

Therefor, in accordance with another aspect of the present invention, vitamin E (free 2R, 4'R, 8'R-alpha tocopherol) may be optionally included in invention compositions in a wide range of concentrations. Any pharmaceutically and physiologically acceptable amount can be employed in the practice of the present invention. In one embodiment of the present invention, when vitamin E is included in invention compositions, vitamin E is present in the range of about 100 up to about 800 I.U. per daily dose. In a preferred embodiment, about 400 I.U. of vitamin E is contained per daily dose.

In addition to vitamin E, alpha lipoic acid is one of the most powerful antioxidants and is a coenzyme required to breakdown sugars, such as glucose, for energy metabolism. Thus, alpha lipoic acid plays an important role in the metabolism of glucose. In addition, alpha lipoic acid helps the body recycle and renew other antioxidants, such as vitamins C and E, Co-Q10, and glutathione.

Therefor, in accordance with another aspect of the present invention, compositions are provided as described herein, optionally containing alpha-lipoic acid, in a wide range of concentrations. Any pharmaceutically and physiologically acceptable amount of alpha-lipoic acid can be employed in the practice of the present invention. In one embodiment of the present invention, when alpha-lipoic acid is included in invention compositions, alpha lipoic acid is present in the range of about 10 mg up to about 600 mg per dose. A preferred embodiment of the present invention contains about 50 mg alpha lipoic acid per daily dose.

It is well recognized that elevated blood homocysteine levels are an indepedent and powerful cardiovascular risk factor. Elevated homocysteine has been postulated to injure arterial endothelial cells, affect platelet-endothelial cell interactions, and cause thrombosis. These effects can complicate or exacerbate the artherogenic process in diabetic patients. High homocysteine can often be normalized by folic acid treatment, thereby aleviating some of these adverse effects.

Therefor, in accordance with another aspect of the present invention, compositions are provided as described herein, optionally containing folate (folic acid) in a wide range of concentrations. Any pharmaceutically and physiologically acceptable amount can be employed in compositions of the present invention. In one embodiment of the present invention, when folate is included in invention compositions, folate is present in the range of about 200 μg up to about 600 μg per dose. A preferred embodiment of the present invention contains about 400 μg folate per dose.

The active components described for use herein can be included in a pharmaceutically suitable vehicle, selected to render such compositions amenable to delivery by oral, rectal, parenteral (e.g., intravenous, intramuscular, intraarterial, intraperitoneal, and the like), or inhalation routes, osmotic pump, and the like.

Pharmaceutical compositions contemplated for use in the practice of the present invention can be used in the form of a solid, a solution, an emulsion, a dispersion, a micelle, a liposome, and the like, wherein the resulting composition contains one or more of the active compounds contemplated for use herein, as active ingredients thereof, in admixture with an organic or inorganic carrier or excipient suitable for nasal, enteral or parenteral applications. The active ingredients may be compounded, for example, with the usual non-toxic, pharmaceutically and physiologically acceptable carriers for tablets, pellets, capsules, troches, lozenges, aqueous or oily suspensions, dispersible powders or granules, suppositories, solutions, emulsions, suspensions, hard or soft capsules, caplets or syrups or elixirs and any other form suitable for use. The carriers that can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents may be used. The active compounds contemplated for use herein are included in the pharmaceutical composition in an amount sufficient to produce the desired effect upon the target process, condition or disease.

In addition, such compositions may contain one or more agents selected from flavoring agents (such as peppermint, oil of wintergreen or cherry), coloring agents, preserving agents, and the like, in order to provide pharmaceutically elegant and palatable preparations. Tablets containing the active ingredients in admixture with non-toxic pharmaceutically acceptable excipients may also be manufactured by known methods. The excipients used may be, for example, (1) inert diluents, such as calcium carbonate, lactose, calcium phosphate, sodium phosphate, and the like; (2) granulating and disintegrating agents, such as corn starch, potato starch, alginic acid, and the like; (3) binding agents, such as gum tragacanth, corn starch, gelatin, acacia, and the like; and (4) lubricating agents, such as magnesium stearate, stearic acid, talc, and the like. The tablets may be uncoated or they may be coated by known techniques to delay disintegration and absorption in the gastrointestinal tract, thereby providing sustained action over a longer period. For example, a time delay material such as glyceryl monostearate or glyceryl distearate may be employed. The tablets may also be coated by the techniques described in the U.S. Pat. Nos. 4,256,108; 4,160,452; and 4,265,874, incorporated herein by this reference, to form osmotic therapeutic tablets for controlled release.

When formulations for oral use are in the form of hard gelatin capsules, the active ingredients may be mixed with an inert solid diluent, for example, calcium carbonate, calcium phosphate, kaolin, or the like. They may also be in the form of soft gelatin capsules wherein the active ingredients are mixed with water or an oil medium, for an example, peanut oil, liquid paraffin, olive oil and the like.

The pharmaceutical compositions may be in the form of a sterile injectable suspension. Such a suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,4-butanediol. Sterile, fixed oils are conventionally employed as a solvent or suspending medium. For this purpose, any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

Compositions contemplated for use in the practice of the present invention may also be administered in the form of suppositories for rectal administration of the active ingredients. These compositions may be prepared by mixing the active ingredients with a suitable non-irritating excipient, such as cocoa butter, synthetic glyceride esters of polyethylene glycols (which are solid at ordinary temperatures, but liquify and/or dissolve in the rectal cavity to release the active ingredients), and the like.

In addition, sustained release systems, including semipermeable polymer matrices in the form of shaped articles (e.g., films or microcapsules) can also be used for the administration of the active compound employed herein.

In accordance with another aspect of the present invention, there are provided methods for the treatment of a subject having diabetes mellitus, said method comprising administering to said subject an effective amount of a composition comprising metformin and one or more of a bioavailable source of chromium, vanadium, or magnesium, or a pharmaceutically acceptable salt thereof, and a physiologically acceptable carrier. All combinations, sources and amounts of the active ingredients discussed herein in conjunction with the compositions of the present invention are contemplated as being administered in accordance with the methods disclosed herein.

In accordance with another embodiment of the present invention there are provided methods for the treatment of a subject having diabetes mellitus, said method comprising administering to said subject an effective amount of a composition comprising metformin and one or more of a bioavailable source of chromium, vanadium, or magnesium, or a pharmaceutically acceptable salt thereof, and a physiologically acceptable carrier, said method further comprising monitoring said subject's HbA1c levels.

As will be appreciated by those of skill in the art, diabetes presents a complicated array of conditions and symptoms including abnormal glucose metabolism, insulin resistance, hyperinsulinemia, hyperglycemia, hypertriglyceridemia, elevated LDL, lowered HDL and elevated blood pressure. Because of the interrelatedness of these conditions and symptoms, invention compositions are useful in treating many of them.

In addition, there are a number of precursor conditions which portend the development of diabetes and which can be treated by administration of invention compositions as described herein. Therefor, in accordance with another aspect of the present invention, there are provided methods for reducing or minimizing elevated HbA1c levels, reducing the dosage of insulin and other anti-diabetic agents described herein, improving glucose metabolism, treating insulin resistance syndrome, decreasing hyperglycemia, regulating blood sugar, for reducing or treating or minimizing daily blood glucose fluctuations, treating or reducing elevated blood pressure, lowering serum triglycerides and cholesterol, and managing other symptoms or conditions associated with perturbations in glucose metabolism, wherein said methods comprise adminstration of invention compositions as described herein.

Therefore, in accordance with another aspect of the present invention, there are provided methods for improving the ability of a subject to metabolize glucose, said method comprising administering to said subject a a glucose metabolism enhancing amount of a composition comprising metformin and one or more of a bioavailable source of chromium, vanadium, or magnesium, a pharmaceutically acceptable salt thereof, and a physiologically acceptable carrier. All combinations, sources and amounts of the active ingredients discussed herein in conjunction with the compositions of the present invention are contemplated as being administered in accordance with this method.

In accordance with another aspect of the present invention, there are provided methods for treating a subject susceptible to daily glucose level fluctuations, said method comprising administering to said subject a glucose level stabilizing amount of a composition comprising metformin and one or more of a bioavailable source of chromium, vanadium, or magnesium, a pharmaceutically acceptable salt thereof, and a physiologically acceptable carrier. All combinations, sources and amounts of the active ingredients discussed herein in conjunction with the compositions of the present invention are contemplated as being administered in accordance with this method.

In accordance with another aspect of the present invention, there are provided methods for treating a subject having hyperglycemia, said method comprising administering to said subject a hyperglycemia reducing amount of a composition comprising metformin and one or more of a bioavailable source of chromium, vanadium, or magnesium, a pharmaceutically acceptable salt thereof, and a physiologically acceptable carrier. All combinations, sources and amounts of the active ingredients discussed herein in conjunction with the compositions of the present invention are contemplated as being administered in accordance with this method.

In accordance with another aspect of the present invention there are provided methods for regulating blood sugar levels in a subject susceptible to abnormal fluctuations in blood sugar levels, said method comprising administering to said subject blood sugar level stabilizing amount of a composition comprising metformin and one or more of a bioavailable source of chromium, vanadium, or magnesium, a pharmaceutically acceptable salt thereof, and a physiologically acceptable carrier. All combinations, sources and amounts of the active ingredients discussed herein in conjunction with the compositions of the present invention are contemplated as being administered in accordance with this method.

In accordance with another aspect of the present invention there are provided methods for treating a subject having insulin resistance syndrome, said method comprising administering to said subject an insulin sensitizing amount of a composition comprising metformin and one or more of a bioavailable source of chromium, vanadium, or magnesium, a pharmaceutically acceptable salt thereof, and a physiologically acceptable carrier. All combinations, sources and amounts of the active ingredients discussed herein in conjunction with the compositions of the present invention are contemplated as being administered in accordance with this method.

In accordance with another aspect of the present invention there are provided methods for treating a subject having higher than normal LDL levels, said method comprising administering to said subject an LDL lowering amount of a composition comprising metformin and one or more of a bioavailable source of chromium, vanadium, or magnesium, a pharmaceutically acceptable salt thereof, and a physiologically acceptable carrier. All combinations, sources and amounts of the active ingredients discussed herein in conjunction with the compositions of the present invention are contemplated as being administered in accordance with this method.

In accordance with another aspect of the present invention there are provided methods for treating a subject having lower than normal HDL levels, said method comprising administering to said subject an HDL raising amount of a composition comprising metformin and one or more of a bioavailable source of chromium, vanadium, or magnesium, a pharmaceutically acceptable salt thereof, and a physiologically acceptable carrier. All combinations, sources and amounts of the active ingredients discussed herein in conjunction with the compositions of the present invention are contemplated as being administered in accordance with this method.

In accordance with another aspect of the present invention there are provided methods for treating a subject higher than normal serum triglyceride levels, said method comprising administering to said subject a serum triglyceride reducing amount of a composition comprising metformin and one or more of a bioavailable source of chromium, vanadium, or magnesium, a pharmaceutically acceptable salt thereof, and a physiologically acceptable carrier. All combinations, sources and amounts of the active ingredients discussed herein in conjunction with the compositions of the present invention are contemplated as being administered in accordance with this method.

In accordance with another aspect of the present invention there are provided methods for treating a subject having elevated blood pressure, said method comprising administering to said subject blood pressure lowering amount of a composition comprising metformin and one or more of a bioavailable source of chromium, vanadium, or magnesium, a pharmaceutically acceptable salt thereof, and a physiologically acceptable carrier. All combinations, sources and amounts of the active ingredients discussed herein in conjunction with the compositions of the present invention are contemplated as being administered in accordance with this method.

In accordance with another aspect of the present invention there are provided methods for reducing the doseage of anti-diabetic medication such as a thiazolidinedione, a sulfonylurea, an α-glucosidase inhibitor or a benzoic acid derivative, said method comprising administering to said subject an effective amount of a composition comprising metformin and one or more of a bioavailable source of chromium, vanadium, or magnesium, a pharmaceutically acceptable salt thereof, and a physiologically acceptable carrier. Optionally, said method further comprises monitoring the subject's blood glucose levels. All combinations, sources and amounts of the active ingredients discussed herein in conjunction with the compositions of the present invention are contemplated as being administered in accordance with this method.

In accordance with another aspect of the present invention, there is provided an improvement over methods for the treatment of a subject having diabetes by administering to said subject an effective amount of insulin, the improvement comprising administering to said subject an insulin need reducing amount of a composition comprising metformin and one or more of a bioavailable source of chromium, vanadium, or magnesium, a pharmaceutically acceptable salt thereof, and a physiologically acceptable carrier. Optionally, said method further comprises monitoring the subject's blood glucose levels. All combinations, sources and amounts of the active ingredients discussed herein in conjunction with the compositions of the present invention are contemplated as being administered in accordance with this method.

Since individual subjects may present a wide variation in severity of symptoms and each active ingredient has its unique therapeutic characteristics, it is up to the practitioner to determine a subject's response to treatment and vary the dosages of the active ingredients accordingly.

All publications, including patent documents, referenced herein are hereby incorporated by this reference to the same extent as if each publication was individually incorporated by reference. The invention will now be described in greater detail by reference to the following non-limiting examples.

Example 1
Effect of Administration of Invention Composition to Patient with Diabetes To test the efficacy of invention compositions, a supplement (detailed below) was administered daily to a female with type II diabetes who was experiencing poor blood sugar control while taking metformin 500 mg b.i.d.

In conjunction with continued metformin administration, the patient was given an oral daily nutritional supplement comprising the following active ingredients:

| | |
|---|---|
| Chromium | 333 μg (in the form of 1 mg Cr-picolinate) |
| Magnesium | 46 mg (in the form of 384 mg MgCl) |
| Vanadyl-sulfate hydrate | 100 mg |
| Vitamin E | 400 I.U. |
| Folate | 400 μg |

TABLE 1

| Therapeutic | HbA1c | Estimated Blood Sugar | Fasting Blood Sugar |
|---|---|---|---|
| Metformin | 9.7 | 200 | 185 |
| Metformin & Supplement (after 2 months) | 7.9 | 141 | 153 |

The above results indicate the degree to which a composition according to the present invention, administered in accordance with invention methods, can dramatically improve blood sugar control and reduce HbA1c levels when compared to treatment with metformin alone.

In addition to the lowered HbA1c and fasting blood sugar levels, the patient experienced a significant lowering of total cholesterol and a concomitant lowering of triglyceride, HDL and LDL levels, as summarized in Table 2, below.

TABLE 2

| Therapeutic | Cholesterol | LDL | HDL | Triglycerides |
|---|---|---|---|---|
| Metformin | 229 | 133 | 52 | 220 |
| Metformin & Supplement (after 2 months) | 192 | 114 | 38 | 200 |

The results summarized in Table 2 indicate that a composition according to the present invention, administered in accordance with invention methods, also dramatically reduces overall cholesterol levels, improves the LDL:HDL ratio and lowers serum triglyeceride levels when compared to treatment with metformin alone.

Example 2
Effect of Administration of Invention Composition to Patient with Diabetes To further test the efficacy of invention compositions, a supplement (detailed below) was administered daily to a 27 year old female with type II diabetes who was experiencing poor blood sugar control while taking metformin 1000 mg b.i.d.

In conjunction with continued metformin administration, the patient was given an oral daily nutritional supplement comprising the following active ingredients:

| | |
|---|---|
| Chromium | 333 μg (in the form of 1 mg Cr-picolinate) |
| Magnesium | 46 mg (in the form of 384 mg MgCl) |
| Vanadyl-sulfate hydrate | 100 mg |
| Vitamin E | 400 I.U. |
| Folate | 400 μg |

After 3 months of augmenting the daily regimen of 1000 mg metformin with the above oral nutritional supplement, the patient's HbA1c level dropped from 8.3 to 6.1. These results again serve to demonstrate the degree to which invention compostions, administered in accordance with invention methods serves to beneficially lower a diabetic pateient's HbA1c levels, even though the patient had experienced poor blood glucose control on elevated levels of metformin alone.

As will be recognized by those skilled in the art, the various embodiments described herein are provided by way of illustration and not limitation; various modifications and substitutions may be made thereto without departing from the spirit and scope of the invention. Such modifications and substitutions are contemplated as within the scope of the following claims.

That which is claimed is:

1. A composition for the treatment of diabetes, said composition comprising metformin; one or more of a bioavailable source of magnesium and pharmaceutically acceptable salts thereof; one or more of a bioavailable source of chromium and pharmaceutically acceptable salts thereof; and one or more of a bioavailable source of vanadium and pharmaceutically acceptable salts thereof; which components synergistically treat diabetes.

2. A composition according to claim 1, wherein said bioavailable source of chromium is one or more of chromium picolinate or chromium polynicotinate.

3. A composition according to claim 1, wherein said bioavailable source of vanadium is vanadyl sulfate.

4. A composition according to claim 1, wherein said bioavailable source of magnesium is magnesium chloride or a magnesium chloride containing complex comprising citrate, fumarate, malate, glutarate, and succinate.

5. A composition according to claim 1, further comprising one or more of aspirin, a bioavailable source of vitamin E, a bioavailable source of α-lipoic acid or a bioavailable source of folic acid.

6. A composition according to claim 1, wherein the amount of metformin is in the range of about 100 mg up to about 2550 mg per dose.

7. A composition according to claim 2, wherein the amount of chromium polynicotinate is from about 30 μg up to about 5000 μg, per dose.

8. A composition according to claim 2, wherein the amount of chromium picolinate is from about 30 μg up to about 1000 μg, per dose.

9. A composition according to claim 3, wherein the amount of vanadyl sulfate is in the range of about 20 mg up to about 100 mg, per dose.

10. A composition according to claim 4, wherein the amount of said magnesium chloride containing complex is in the range of about 200 mg up to about 400 mg, per dose.

11. A composition according to claim 4, wherein the amount of magnesium chloride is in the range of about 300 mg up to about 400 mg, per dose.

12. A composition according to claim 1, wherein the amount of said bioavailable magnesium is in the range of about 10 mg up to about 60 mg, per dose.

13. A composition according to claim 5, wherein the amount of aspirin is in the range of about 10 mg up to about 100 mg, per dose.

14. A composition according to claim 5, wherein the amount of vitamin E is in the range of about 400 up to about 800 I.U. per dose.

15. A composition according to claim 5, wherein the amount of folic acid is in the range of about 400 μg up to about 1000 μg per dose.

16. A composition according to claim 5, wherein the amount of α-lipoic acid is less than about 600 mg per dose.

17. A composition according to claim 1, wherein said pharmaceutically acceptable salt is one or more of sodium, potassium, lithium, calcium, magnesium, zinc, or iron.

18. A composition according to claim 1, further comprising an effective amount of one or more anti-diabetic agents.

19. A composition according to claim 18, wherein said anti-diabetic agent is insulin, a thiazolidinedione, a sulfonylurea, an α-glucosidase inhibitor or a benzoic acid derivative.

20. A composition according to claim 19, wherein said sulfonylurea is acetohexamide, chlorpropamide, tolazimide, tolbutamide, glycazide, glipizide, glyburide, or glimeperide.

21. A composition according to claim 19, wherein said thiazolidinedione is troglitazone.

22. A composition according to claim 19, wherein said α-glucosidase inhibitor is acarbose, or miglitol.

23. A composition according to claim 19, wherein said benzoic acid derivative is repaglinide.

24. A composition according to claim 1, wherein said composition is in the form of a tablet, a troche, a lozenge, an aqueous or oily suspension, a dispersible powder or granules, an emulsion, a hard or soft capsule, a caplet, a syrup or elixir, a suppository, an aerosol, or a sterile injectable suspension.

25. A method for the treatment of diabetes mellitus in a subject having diabetes mellitus, said method comprising administering to said subject an effective amount of a composition comprising metformin; one or more of a bioavailable source of magnesium and pharmaceutically acceptable salts thereof; one or more of a bioavailable source of chromium and pharmaceutically acceptable salts thereof; and one or more of a bioavailable source of vanadium and pharmaceutically acceptable salts thereof; which components synergistically treat diabetes mellitus.

26. A method according to claim 25, wherein said administration is oral, parenteral, rectal, sublingual, or via inhalation.

27. A method according to claim 25, wherein said physiologically acceptable carrier is suitable for oral, parenteral, rectal, sublingual or inhalation administration.

28. A method according to claim 25, wherein said method further comprises monitoring said subject's HbA1c levels.

29. A method for treating elevated HbA1c levels in a subject having elevated HbA1c levels, said method comprising administering to said subject an effective amount of a composition comprising metformin; one or more of a bioavailable source of magnesium and pharmaceutically acceptable salts thereof; one or more of a bioavailable source of chromium and pharmaceutically acceptable salts thereof; and one or more of a bioavailable source of vanadium and pharmaceutically acceptable salts thereof; which components synergistically treat elevated HbA1c levels in a subject having elevated HbA1c levels.

30. A method for treating daily blood glucose fluctuations in a subject susceptible to daily blood glucose fluctuations, said method comprising administering to said subject an effective amount of a composition comprising metformin; one or more of a bioavailable source of magnesium and pharmaceutically acceptable salts thereof; one or more of a bioavailable source of chromium and pharmaceutically acceptable salts thereof; and one or more of a bioavailable source of vanadium and pharmaceutically acceptable salts thereof; which components synergistically treat daily blood glucose fluctuations in a subject susceptible to daily blood glucose fluctuations.

31. A method for improving the ability of a subject to metabolize glucose, said method comprising administering to said subject an effective amount of a composition comprising metformin; one or more of a bioavailable source of magnesium and pharmaceutically acceptable salts thereof; one or more of a bioavailable source of chromium and pharmaceutically acceptable salts thereof; and one or more of a bioavailable source of vanadium and pharmaceutically acceptable salts thereof; which components synergistically improve the ability of a subject to metabolize glucose.

32. A method for reducing blood sugar levels in a subject susceptible to abnormal fluctuations in blood sugar levels, said method comprising administering to said subject a hyperglycemia reducing amount of a composition comprising metformin; one or more of a bioavailable source of magnesium and pharmaceutically acceptable salts thereof; one or more of a bioavailable source of chromium and pharmaceutically acceptable salts thereof; and one or more of a bioavailable source of vanadium and pharmaceutically acceptable salts thereof; which components synergistically reduce blood sugar levels in a subject susceptible to abnormal fluctuations in blood sugar levels.

33. A method for treating hyperglycemia in a subject having hyperglycemia, said method comprising administering to said subject a hyperglycemia reducing amount of a composition comprising metformin; one or more of a bioavailable source of magnesium and pharmaceutically acceptable salts thereof; one or more of a bioavailable source of chromium and pharmaceutically acceptable salts thereof; and one or more of a bioavailable source of vanadium and pharmaceutically acceptable salts thereof; which components synergistically treat hyperglycemia in a subject having hyperglycemia.

34. A method for treating insulin resistance syndrome in a subject having insulin resistance syndrome, said method comprising administering to said subject an insulin sensitizing amount of a composition comprising metformin; one or more of a bioavailable source of magnesium and pharmaceutically acceptable salts thereof; one or more of a bioavailable source of chromium and pharmaceutically acceptable salts thereof; and one or more of a bioavailable source of vanadium and pharmaceutically acceptable salts thereof; which components synergistically treat insulin resistance syndrome in a subject having insulin resistance syndrome.

35. A method for reducing the dosage of anti-diabetic medication needed for treatment of a diabetic subject, said method comprising administering to said subject an effective amount of a composition comprising metformin; one or more of a bioavailable source of magnesium and pharmaceutically acceptable salts thereof; one or more of a bioavailable source of chromium and pharmaceutically acceptable salts thereof; and one or more of a bioavailable source of vanadium and pharmaceutically acceptable salts thereof; which components synergistically reduce the dosage of anti-diabetic medication needed for treatment of a diabetic subject.

36. A method according to claim 35, wherein said anti-diabetic medication is one or more of insulin, a thiazolidinedione, a sulfonylurea, an α-glucosidase inhibitor or a benzoic acid derivative.

37. A method according to claim 35, further comprising monitoring said subject's blood glucose levels.

38. In a method for the treatment of diabetes in a subject having diabetes by administering to said subject an effective amount of insulin, the improvement comprising administering to said subject an insulin need reducing amount of a composition comprising metformin; one or more of a bioavailable source of magnesium and pharmaceutically acceptable salts thereof; one or more of a bioavailable source of chromium and pharmaceutically acceptable salts thereof; and one or more of a bioavailable source of vanadium and pharmaceutically acceptable salts thereof; which components of said composition synergistically reduce the effective amount of insulin needed.

39. A composition according to claim 1, wherein the amount of said bioavailable magnesium is in the range 10 mg up to about 3 gm, per dose.

40. A composition according to claim 1, wherein the amount of said bioavailable magnesium is in the range 10 mg up to about 1500 mg, per dose.

* * * * *